(12) United States Patent
Hayden et al.

(10) Patent No.: US 8,506,639 B2
(45) Date of Patent: Aug. 13, 2013

(54) SLIDING PATELLAR PROSTHESIS

(75) Inventors: Adam Iredell Hayden, Fort Wayne, IN (US); Luke Aram, Warsaw, IN (US); Dan Auger, Fort Wayne, IN (US); Jordan Soonja Lee, Warsaw, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 1838 days.

(21) Appl. No.: 10/814,097

(22) Filed: Mar. 31, 2004

(65) Prior Publication Data

US 2005/0222685 A1 Oct. 6, 2005

(51) Int. Cl.
*A61F 2/38* (2006.01)

(52) U.S. Cl.
USPC .................................................... 623/20.14

(58) Field of Classification Search
USPC ............... 623/13.12–13.2, 20.14–20.36
See application file for complete search history.

(56) References Cited

U.S. PATENT DOCUMENTS

| | | | |
|---|---|---|---|
| 3,806,961 A | 4/1974 | Müller | |
| 3,878,566 A * | 4/1975 | Bechtol | 623/20.19 |
| 4,007,495 A * | 2/1977 | Frazier | 623/20.19 |
| 4,094,017 A * | 6/1978 | Matthews et al. | 623/20.22 |
| 4,151,615 A * | 5/1979 | Hall | 623/20.19 |
| 4,158,894 A * | 6/1979 | Worrell | 623/20.18 |
| 4,285,070 A * | 8/1981 | Averill | 623/20.2 |
| 4,309,778 A | 1/1982 | Buechel et al. | |
| 4,340,978 A | 7/1982 | Buechel et al. | |
| 4,344,192 A | 8/1982 | Imbert | |
| 4,353,135 A | 10/1982 | Forte et al. | |
| 4,470,158 A | 9/1984 | Pappas et al. | |
| 4,888,021 A | 12/1989 | Forte et al. | |
| 4,944,756 A | 7/1990 | Kenna | |
| 5,019,104 A * | 5/1991 | Whiteside et al. | 623/20.2 |
| 5,021,061 A | 6/1991 | Wevers et al. | |
| 5,197,986 A | 3/1993 | Mikhail | |
| 5,236,462 A * | 8/1993 | Mikhail | 623/20.2 |
| 5,246,460 A | 9/1993 | Goodfellow et al. | |
| 5,314,480 A * | 5/1994 | Elloy et al. | 623/20.2 |
| 5,326,361 A | 7/1994 | Hollister | |
| 5,358,529 A | 10/1994 | Davidson | |

(Continued)

FOREIGN PATENT DOCUMENTS

| | | |
|---|---|---|
| EP | 0 670 151 | 9/1995 |
| FR | 2663839 | 1/1992 |

(Continued)

OTHER PUBLICATIONS

Notification of Reasons for Refusal (Translation) corresponding to Japanese patent application 2005-099386, mailing date Jan. 4, 2011 (4 pages).

*Primary Examiner* — David Isabella
*Assistant Examiner* — Ann Schillinger
(74) *Attorney, Agent, or Firm* — Maginot, Moore & Beck LLP

(57) ABSTRACT

An improved sliding patellar replacement component is provided. Various combinations of translational and/or rotational degrees of freedom are provided by boss and channel configurations between the base subcomponent of the replacement component and the articulating subcomponent of the patellar replacement component. In one embodiment, spin about one axis is restricted by a spin stop that may be movable to allow for ease of assembly. Alternatively, the boss and channel are configured to function as a spin stop. Assembly of the patellar replacement component in one embodiment is simplified by the provision of a boss assembly region.

21 Claims, 15 Drawing Sheets

(56) References Cited

U.S. PATENT DOCUMENTS

| | | | |
|---|---|---|---|
| 5,480,443 A * | 1/1996 | Elias | 623/20.18 |
| 5,571,196 A | 11/1996 | Stein | |
| 5,593,450 A | 1/1997 | Scott et al. | |
| 5,609,644 A * | 3/1997 | Ashby et al. | 623/20.2 |
| 5,702,459 A | 12/1997 | Hummer et al. | |
| 5,702,465 A * | 12/1997 | Burkinshaw | 623/20.2 |
| 5,723,016 A | 3/1998 | Minns et al. | |
| 5,738,686 A | 4/1998 | Kubein-Meesenburg et al. | |
| 5,824,098 A | 10/1998 | Stein | |
| 5,824,099 A | 10/1998 | Mendes et al. | |
| 5,871,540 A | 2/1999 | Weissman et al. | |
| 5,879,394 A * | 3/1999 | Ashby et al. | 623/20.33 |
| 6,146,423 A * | 11/2000 | Cohen et al. | 623/20.2 |
| 6,315,798 B1 * | 11/2001 | Ashby et al. | 623/20.17 |
| 6,602,292 B2 * | 8/2003 | Burkinshaw | 623/20.2 |
| 2001/0037155 A1 | 11/2001 | Merchant | |
| 2002/0128719 A1 | 9/2002 | Burkinshaw | |
| 2003/0033018 A1 | 2/2003 | Merchant | |
| 2003/0088315 A1 * | 5/2003 | Supinski | 623/20.2 |
| 2003/0120346 A1 | 6/2003 | Mercinek et al. | |
| 2004/0143336 A1 * | 7/2004 | Burkinshaw | 623/20.15 |
| 2004/0236428 A1 * | 11/2004 | Burkinshaw et al. | 623/20.15 |
| 2004/0254645 A1 * | 12/2004 | Arnin et al. | 623/20.2 |

FOREIGN PATENT DOCUMENTS

| | | |
|---|---|---|
| FR | 2 706 286 | 12/1994 |
| JP | 50155092 | 12/1975 |
| JP | 2008508190 | 3/2008 |
| JP | 2008080311 | 4/2008 |

* cited by examiner

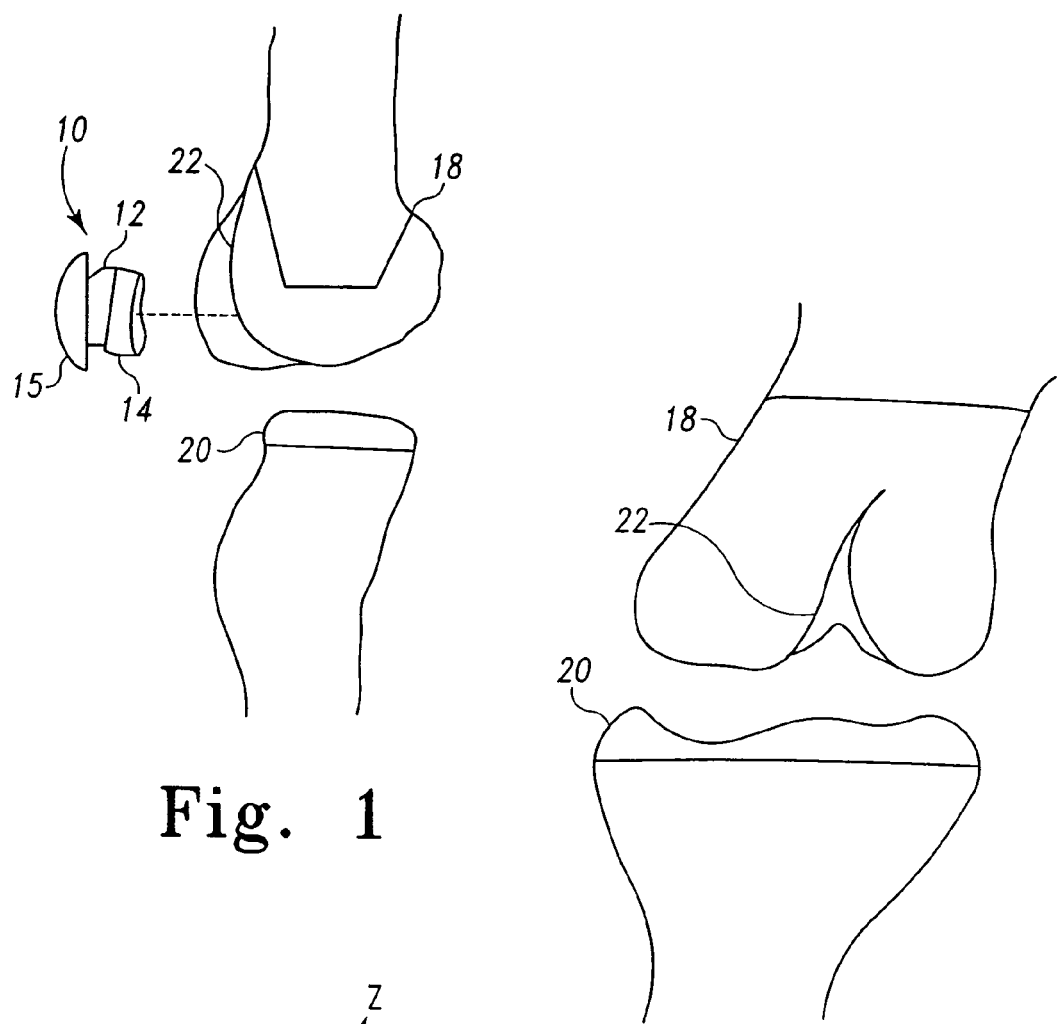
Fig. 1
Fig. 2
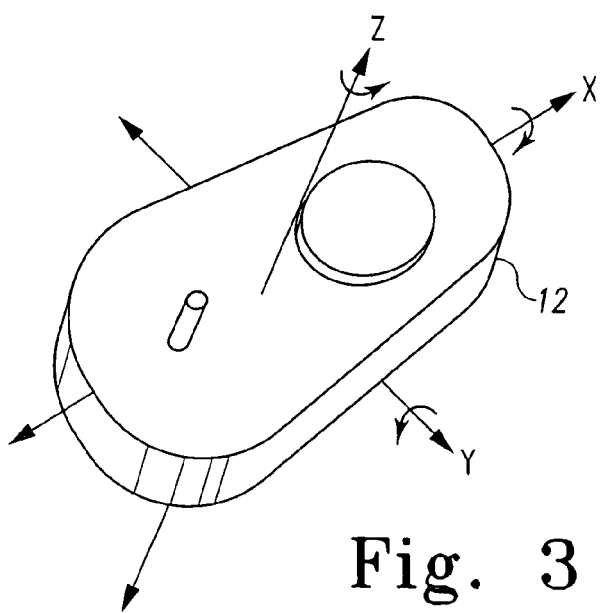
Fig. 3

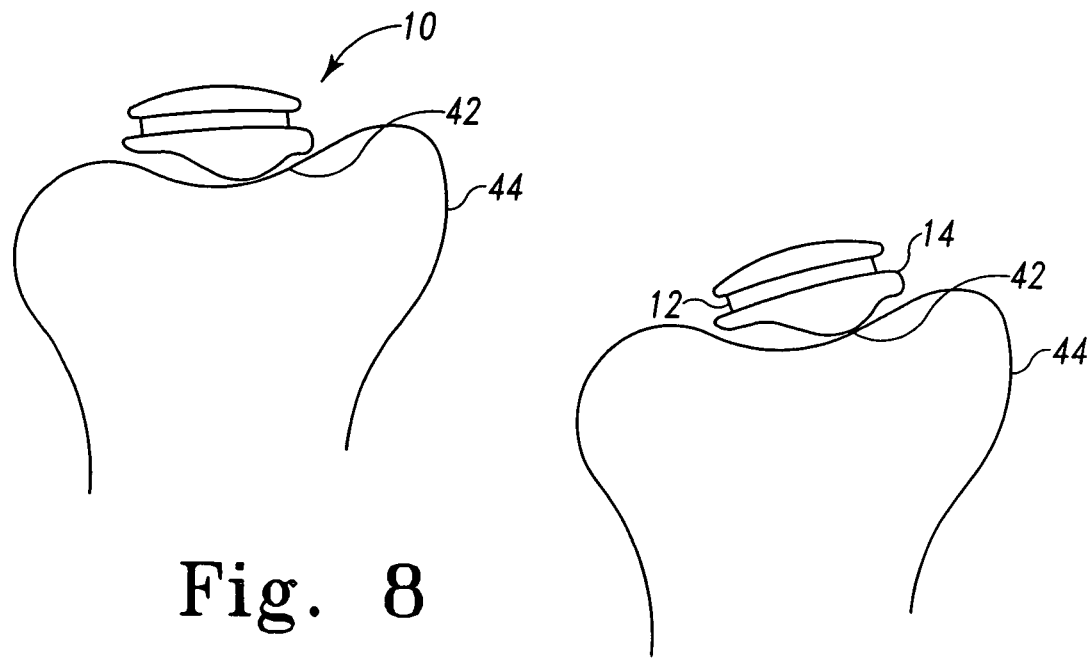
Fig. 8
Fig. 9
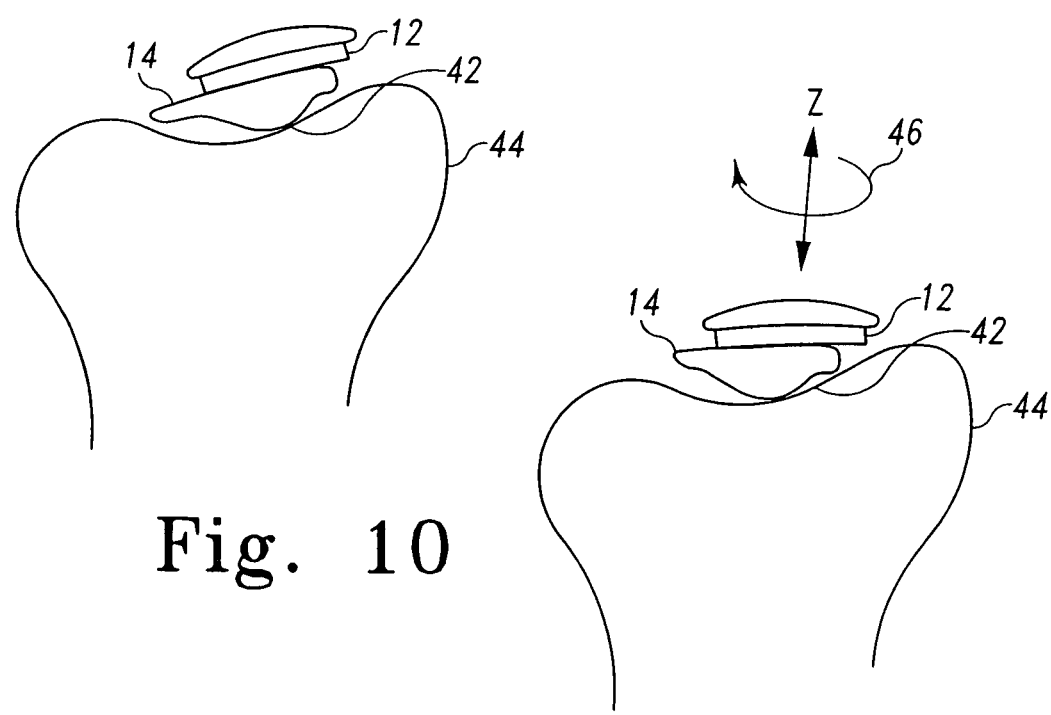
Fig. 10
Fig. 11

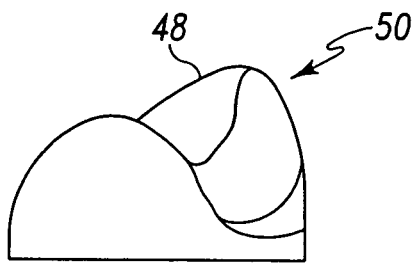 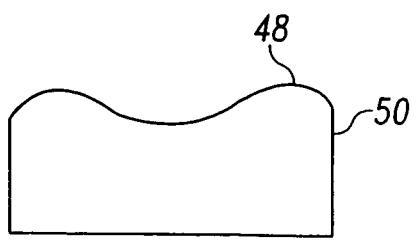
Fig. 12  Fig. 13
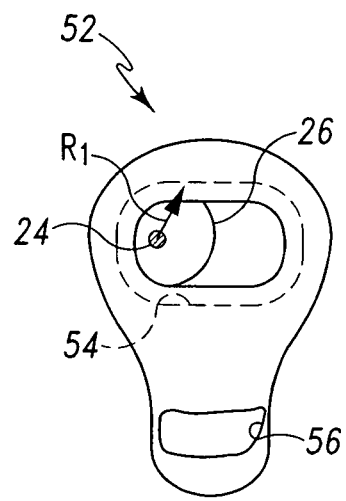
Fig. 14

SLIDING PATELLAR PROSTHESIS

FIELD OF THE INVENTION

The present invention relates to prosthetic components, and particularly to a patellar prosthesis.

BACKGROUND OF THE INVENTION

Implantable knee prostheses for diseased and/or damaged knees typically include three components, namely a femoral component, a tibial component and a meniscal component. The femoral component may also include a patellar surface. The patella bone may be resurfaced with a prosthesis or left unresurfaced. The prosthesis components are generally configured to restore or emulate as much of the natural motion of the knee joint as possible. The selection of the particular prosthesis components is usually dictated by the condition of the patient's knee. For instance, the condition of the distal end of the femur and proximal end of the tibia, as well as the patency of the surrounding ligaments and soft tissue can affect the form of the joint prosthesis.

Generally, a total knee joint replacement includes a tibial component having a platform portion which replaces the entire superior surface of the tibial plateau and substitutes for the tibial condylar surfaces. The femoral component also includes laterally-spaced condylar portions joined by an inter-condylar bridge and a patellar surface. The inter-condylar bridge is in the form of a groove. The mating surfaces are smoothly curved in the anterior-posterior (AP) direction to generally match the lateral profile of the natural femoral and tibial condyles, and to ultimately replicate the normal joint movement.

A patella typically includes a ridge on its posterior face that separates the medial and lateral facets of the patella. The ridge rides within the inter-condylar groove as the knee is flexed so that the patella tracks along the groove. However, the movement of the various knee components is very complicated, and even shaped replacement components may not perform as well as a healthy, natural patella. For example, fluoroscopic studies have shown that when a leg is flexed to create a ninety degree angle, a natural patella will exhibit a 7 degree tilt. A common replacement patella, however, exhibits a 25 degree tilt.

There are two types of patellar replacement components that are commonly used. One type, which is the most commonly used, is constructed entirely of polyethylene. The other type is made from multiple subcomponents. In a multiple subcomponent patellar replacement component, there will typically be an articulating subcomponent made from polyethylene that is attached to a base. The base is implanted into the resected patella and is constructed from metal. The base in this type of patellar replacement component is of a uniform width while.

Initial implantation of a patellar replacement component is accomplished after resection of the natural patella. Resection is typically performed by first attaching a cutting guide to the patellar bone and cutting the patella along the angle defined by the quadriceps tendon and the patellar tendon as directed by the guide. The replacement component is then attached to the resected patella using a base that has a uniform depth. A problem with this approach is that patellae are not identical from individual to individual, or even from knee to knee in a particular individual. Thus, while the angle defined by quadriceps tendon and the patellar tendon is generally acceptable, it may not be the optimal angle for the particular patella being resected. Thus, when the base is attached, the patellar replacement component is aligned differently with respect to the femur as compared with the natural patella.

Replacement patellar components may not perform as well as natural patellae and can present a variety of undesired results. The misalignment can result in subluxation or dislocation of the patella. This may result in increased cartilage wear and knee pain. Of course, misalignment also results in increased wear of the various components. Another common problem is "patellar clunk syndrome". In a knee exhibiting this syndrome, the patella "snags" as the knee is flexed and then extended resulting in patella displacement. However, as the pressure on patella increases, the snag is overcome, and the patella forcefully moves past the snag, typically impacting another surface. This impact causes pain and may even result in an audible "clunk".

One approach to solving the maltracking problem experienced with replacement patellar components is to use shaped bone contacting surfaces including dome shapes and "saddle" shapes. Saddle shapes resemble hyperbolic paraboloids with two high ends and a low middle. The high ends are designed to track the inter-condylar groove.

Performance of shaped bone contacting surfaces is enhanced by providing for some relative motion between the pieces of the patellar replacement component. Enhanced performance is realized because of the principle that an object being acted upon by an external force will naturally turn until the largest possible area of the object is exposed to such a force. Accordingly, as, for example, a saddle shaped patellar replacement component begins to rotate up and out of the inter-condylar groove, if relative motion between the bone contacting surface and the rest of the replacement component is allowed, the bone contacting surface will not rotate, thus keeping both of the higher ends within the inter-condylar groove. As the force acting upon the patellar replacement component subsides, the bone contacting surface merely settles within the inter-condylar groove.

However, there are a limited number of known modalities for providing a patellar replacement component with some degree of freedom to either translate or rotate. Some replacement components combine some translational capability with rotational capability. However, these replacement parts are very limited in the degrees of rotation and/or translation provided. It would be beneficial to provide a variety of combinations of translational and/or rotational movement between pieces of a patellar replacement component.

Moreover, in order to allow relative motion between the various parts of a patellar replacement component, some assembly is needed. Of course, some assembly of patellar replacement component is commonly performed in order to use different types of material in the component. More specifically, the base is typically made of a material such as cobalt chrome alloys, although other materials such as ceramics, carbon based alloys or titanium alloys may be used. The bone contacting surface is made of polyethylene or ceramics. Nonetheless, assembly of moving parts presents additional design considerations. For example, the fit of the parts must be loose enough so that movement is not hindered, but the assembled parts must nonetheless be securely joined.

Additionally, some allowance must be made for the replacement of parts that have worn out after implantation. For example, it is useful to merely replace the bone contacting surface of a patellar replacement component than to replace the entire patellar component. Such limited replacement, however, is normally done within an incision area. Thus, it would be beneficial if a patellar replacement component included parts that could easily be assembled within a constricted space while ensuring that they remain securely assembled.

What is needed therefore is a patellar replacement component which overcomes one or more of the above-mentioned disadvantages.

SUMMARY OF THE INVENTION

It is an object of the invention to provide a sliding patellar replacement component that may be configured to incorporate a variety of combinations of freedom of movement. It is a further object to provide a patellar replacement component with up to three translational and three rotational degrees of freedom. Another object of the invention is to provide for control of spin of a subcomponent of a patellar replacement component with respect to other subcomponents of the replacement component such that the spin is limited to a predetermined range. Yet another object of the invention is to allow for ease of assembly and/or disassembly of the patellar replacement component while minimizing the potential for unintended disassembly.

In one embodiment of the invention, a sliding patellar replacement component includes a base subcomponent, a boss subcomponent and an articulating subcomponent for receiving the boss. The boss and channel configuration is used to allow up to three degrees of rotational freedom or a combination of translational and rotational freedom. The articulating subcomponent is assembled to the boss through a boss assembly region. The boss assembly region may be an area of a retaining region that is more flexible than the remainder of the retaining region. Alternatively, the boss assembly region may be a slot or other opening including a key, through which the head of a boss can be inserted. In one embodiment, a movable spin stop member is used in conjunction with a boss assembly region to facilitate assembly while minimizing the potential for unintended disassembly.

A spin stop member is provided in accordance with another aspect of the invention to allow spin about an axis only within a predetermined range. The spin stop member may be retractable, movable, or rigid. In one embodiment, the spin stop member is provided by a specifically shaped boss and channel configuration.

These objects and certain benefits of the invention can be ascertained from the following written description taken together with the accompanying figures.

DESCRIPTION OF THE FIGURES

FIG. 1 is a partially exploded perspective view of the components of a joint prosthesis that incorporates features of the present invention.

FIG. 2 is a front elevational view of the components of FIG. 1 with the patellar component removed for clarity of description.

FIG. 3 shows a coordinate system referencing the base of the patellar replacement component of FIG. 1.

FIG. 8 shows the patellar replacement component of FIG. 1 within an inter-condylar groove of a femur.

FIG. 9 is a view similar to FIG. 8, but shows the patellar replacement component as it has moved within the inter-condylar groove of the femur.

FIG. 10 is a view similar to FIG. 9, but shows the articulating subcomponent of the patellar replacement component after translation within the inter-condylar groove of the femur.

FIG. 11 is a view similar to FIG. 10, but shows the articulating subcomponent of the patellar replacement component after spinning within the inter-condylar groove of the femur.

FIG. 12 is a perspective view of an alternative embodiment of an articulating subcomponent of a patellar replacement component that incorporates features of the present invention.

FIG. 13 is a side elevational view of the articulating subcomponent of FIG. 12.

FIG. 14 is a bottom elevational view of an alternative embodiment of an articulating subcomponent of a patellar replacement component that incorporates features of the present invention that may be used with the base of FIG. 4.

DESCRIPTION OF THE PREFERRED EMBODIMENTS

Figure 5:
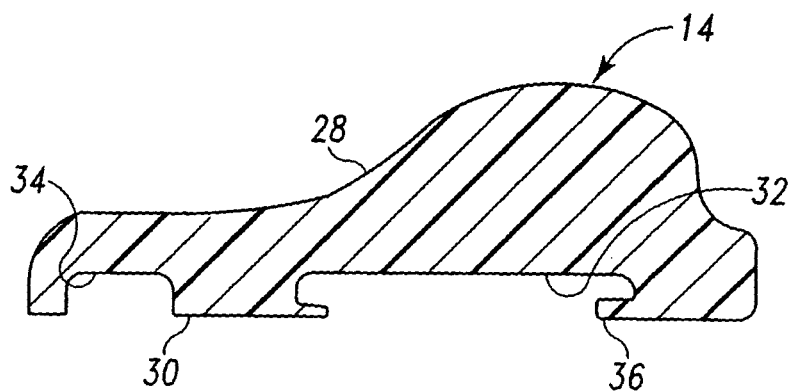
FIG. 5 is a cross sectional view of an articulating subcomponent of a patellar replacement component that incorporates features of the present invention that may be used with the base of FIG. 4.

For the purposes of promoting an understanding of the principles of the invention, reference will now be made to the embodiments illustrated in the drawings and described in the following written description. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring generally to FIG. 1, a knee joint comprising a patellar replacement component 10 is shown. Patellar replacement component 10 includes a plurality of subcomponents including base 12 and articulating subcomponent 14. In this embodiment, base 12 is implanted into resected natural patella 15. Patellar replacement component 10 typically engages femoral component 18 which is located above tibial component 20. Articulating subcomponent 14 of patellar replacement component 10 typically engages femur 18 along inter-condylar groove 22. During flexing of the knee, patellar replacement component moves along inter-condylar groove 22 from the location in FIG. 1 which is generally to the left of femoral component 18, to a position almost directly below femoral component 18.

In accordance with one object of the present invention, relative motion is provided between articulating subcomponent 14 and base 12. Directional relationships within a knee system are typically described with reference to a femorally based coordinate system including anterior-posterior, inferior-superior, and medial-lateral axis. However, because patellar component 10 actually changes orientation during normal motion, it is convenient for further description of the present invention to define a different reference coordinate system. Accordingly, a coordinate system is set forth in FIG. 3 which will be referred to in describing the present invention. With reference to FIG. 3, six degrees of motion are shown. Three degrees of translational motion are defined as motion along the X, Y and Z axis. Similarly, three degrees of rotational motion are defined by rotation about the X, Y and Z axis, indicated by the curved arrows along the respective axis. If the axis of rotation goes through the object that is rotating, then the object is spinning. As used herein, a degree of motion will be defined as motion in the above degrees of motion with reference to the base of the various patellar replacement components.

To provide some context of the above coordinate system with a femorally based coordinate system, when patellar replacement component 10 is located in a flexed left knee, movement along translational axis X corresponds to translation in the medial-lateral direction (generally right to left as shown in FIG. 3), movement along translational axis Y corresponds to translation in the anterior-posterior direction (generally left to right as shown in FIG. 3), and movement along translational axis Z corresponds to translation in the superior-inferior direction (generally upper to lower as shown in FIG. 3).

Figure 4:
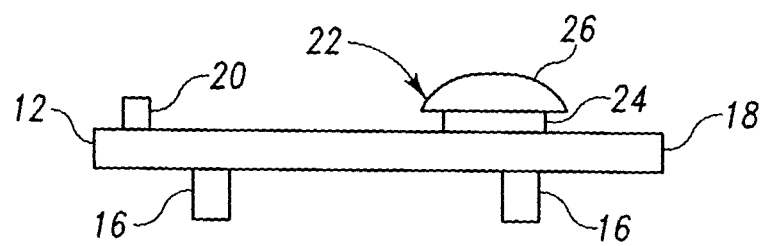
FIG. 4 is a side elevational view of the base of FIG. 1.

Referring now to FIG. 4, a side elevational view of base 12 of patellar replacement component 10 is shown. Base 12 includes pegs 16 which project from platform 18. Pegs 16 are used to attach base 12 to resected natural patella 15. Base 12 further includes spin stop 20 and boss 22. Boss 22 includes stem 24 and head 26 which in this embodiment is generally domed shape.

FIG. 5 is a cross sectional view of articulating subcomponent 14. Articulating subcomponent 14 includes shaped bone contacting surface 28 and bearing surface 30. The shape of bone contacting surface 28 is discussed more fully below. Bearing surface 30 is designed to be supported by the upper surface of platform 18. Articulating subcomponent 14 further includes channel 32 and spin stop receiving chamber 34, both of which open to bearing surface 30. The opening of channel 32 at bearing surface 30 is circumscribed by lip 36.

When articulating subcomponent 14 is assembled onto base 12, spin stop 20 is received within spin stop receiving chamber 34, and bearing surface 30 is adjacent the upper surface of platform 18. Head 26 of boss 22 lies within channel 32, and lip 36 is located underneath head 26 and adjacent stem 24 of boss 22.

Figure 6:
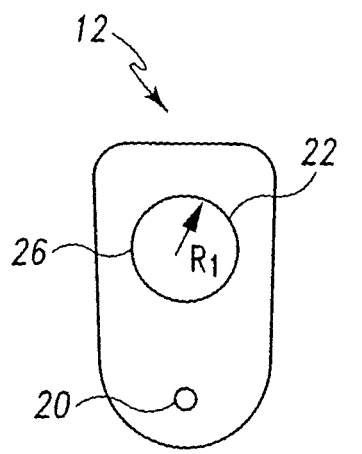
FIG. 6 is a top elevational view of the base of FIG. 4.
Figure 7:
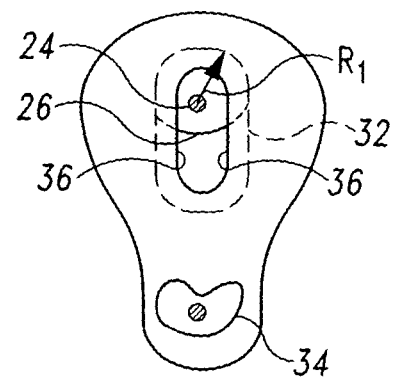
FIG. 7 is a bottom elevational view of the articulating subcomponent of FIG. 5.

FIG. 6 is a top elevational view of base 12, showing the radius of head 26 of boss 22 as $R_1$. Referring now to FIG. 7, which is a cross sectional view of articulating subcomponent 14 assembled onto base 12, a circular dotted line indicates the position of head 22 within channel 32 which is shown as an elliptical dotted line. As indicated by $R_1$, head 26 is restrained within channel 32 by lips 36. In this embodiment, the width of channel 32, less the width of lip 36 on one side of the channel and the width of lip 36 on the opposite side of the channel is slightly larger than the width of stem 24 of boss 22. As shown in FIG. 4, the diameter of head 26 is substantially wider than the width of stem 24.

In the embodiment of FIGS. 4-7, channel 32 is extended along the X-axis. Accordingly, translation of articulating subcomponent 14 in the medial lateral direction is allowed. As articulating subcomponent 14 translates along the X-axis, spin stop 20 moves within spin stop receiving chamber 34 and stem 24 moves within the opening of channel 32 circumscribed by lip 36.

Additionally, because head 26 of boss 22 is circular in the X-Y plane, as shown in FIG. 6, articulating subcomponent 14 is allowed to rotate about boss 22. Thus, articulating subcomponent spins about the Z-axis. However, such spinning is constrained by spin stop 20. Specifically, as articulating subcomponent 14 spins, spin stop receiving chamber 34 moves relative to spin stop 20. As soon as spin stop receiving chamber 34 contacts spin stop 20, continued rotation of articulating subcomponent 14 is not allowed. Thus, spin of articulating subcomponent 14 is limited by the structure that defines the shape of spin stop receiving chamber 34. In the embodiment of FIG. 6, articulating subcomponent 14 is allowed to spin on the order of 15 degrees.

The effect of allowing translation and spin is shown in FIGS. 8-11. FIG. 8 shows patellar replacement component 10 in a tracking position within inter-condylar groove 42 of femoral component 44. FIG. 9 shows patellar replacement component 10 beginning to track out of inter-condylar groove 42 along the X-axis as, for example, the knee is moved from a position of extension to a position of flexion. As patellar replacement component 10 moves out of inter-condylar groove 42, bone contacting surface 28 pushes against the sides of inter-condylar groove 42. Because channel 32 lays in the X-axis, boss 22 is allowed to translate within channel 32. Thus, as shown in FIG. 10, base 12 and the resected patella continue to move to the right along the X-axis, but articulating subcomponent 14 remains within inter-condylar groove 42.

As the above translation is occurring, spinning about the Z-axis may also be occurring. This occurs because as the knee is moving, the position of patellar replacement component 10 within inter-condylar groove 42 is also moving and the cross section of inter-condylar groove 42 is changing. Thus, the surface profile of inter-condylar groove 42 which bone contacting surface 28 is contacting is changing. Accordingly, as bone contacting surface 28 is pushing against the side of inter-condylar groove 42, articulating subcomponent 14 will tend to spin so as to place the largest possible area against the side of inter-condylar groove 42. So long as spin stop 20 is not in contact with a side of spin stop receiving chamber 34, articulating subcomponent 14 will spin. This spinning action operates to maintain a portion of articulating subcomponent 14 within inter-condylar groove 42, improving tracking. This is referred to as a self-correcting feature and its operation is shown by FIGS. 8-11. Note that, as shown in FIG. 11, articulating subcomponent 14 has spun slightly in the direction of arrow 46 in relation to its position in FIG. 10.

As discussed above, the tendency of an object to spin or rotate in reaction to a force exerted against it is very useful in improving the tracking capability of a patellar replacement component. The dome shape of bone contacting surface 28 is only one shape that has been found useful in improving tracking. Another shape that was discussed previously is the saddle shape. A patellar component possessing this shape is discussed in U.S. Pat. No. 4,094,017, the disclosure of which is incorporated herein by reference in its entirety. FIG. 12 shows an articulating subcomponent 50 having a saddle shaped bone contacting surface 48 similar to that disclosed in U.S. Pat. No. 4,094,017. As shown in FIG. 13, articulating subcomponent 50 includes a low center portion and two high end portions. A saddle shaped bone contacting surface is useful even when combined with a base that does not include a spin stop, thus allowing unconstrained rotation about the Z-axis. The present invention is not restricted to a particular bone contacting surface shape and thus includes within its scope such saddle shaped bone contacting surfaces as well as other shapes.

Referring now to FIG. 14, a cross sectional view of an alternative embodiment of an articulating subcomponent assembled onto base 12. Articulating subcomponent 52 operates in a manner very similar to articulating subcomponent 14. The difference is that channel 54 lays along the Y-axis as opposed to the X-axis. Accordingly, translation is allowed in the anterior posterior direction. Just as with articulating subcomponent 14, articulating subcomponent 52 is allowed to spin about the Z-axis, as limited by spin stop 20 and the structure defining spin stop receiving chamber 56.

Figure 15:
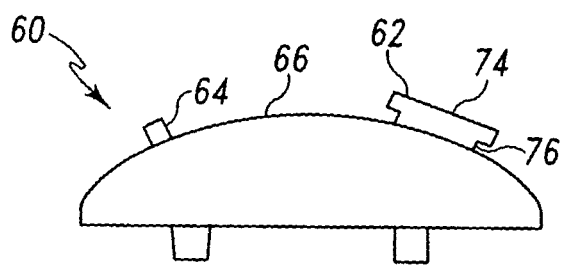
FIG. 15 is a side elevational view of an alternative embodiment of a base of a patellar replacement component that incorporates features of the present invention.
Figure 16:
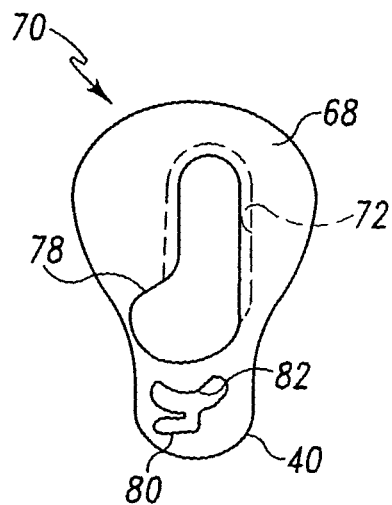
FIG. 16 is a bottom elevational view of an embodiment of an articulating subcomponent of a patellar replacement component that incorporates features of the present invention that may be used with the base of FIG. 15.

Alternative degrees of motion are readily achieved in accordance with the present invention. With reference to FIG. 15, a modified base 60 is shown. Base 60 includes boss 62 and spin stop 64. Upper surface 66 of base 60 is spherically curved. Bearing surface 68 of articulating subcomponent 70 shown in FIG. 16 is curved in a complimentary manner so as to lay adjacent to upper surface 66 when articulating subcomponent 70 is assembled onto base 60. Accordingly, as boss 62 moves along the length of channel 72, a rotational movement is realized, with articulating subcomponent 70 rotating about the Y-axis. Additionally, articulating subcomponent 70 may spin about the Z-axis, as limited by spin stop 64 and the structure defining spin stop receiving chamber 82 in the same manner as discussed above. Thus, two degrees of rotation are achieved.

Instead of rotation about the Y-axis and the Z-axis, the patellar implant can be designed to rotate about the X-axis and the Z-axis. This is accomplished by simply rotating the orientation of the channel by 90 degrees. Thus, the channel would have an orientation similar to the orientation of channel 54 of articulating subcomponent 52 shown in FIG. 14.

Alternatively, a third degree of rotation is possible about the X-axis. This is accomplished by providing channel 72 with a width that is wider than the diameter of head 74 of boss 62, along with providing an opening from channel 72 to bearing surface 68 that is wider than the width of stem 76 of boss 62. Accordingly, relative motion of boss 62 from side to side within channel 72 is allowed. Therefore, because boss 62 is dome shaped, upper surface 66 is curved along the Y-axis. Therefore, movement of boss 62 from side to side within channel 72 is rotation about the X-axis. Of course, head 74 must remain wider than the opening from channel 72 to bearing surface 68 to ensure head 74 is retained within channel 72.

Articulating subcomponent 70 also includes boss assembly region 78 and spin stop chamber loading region 80 which is in communication with spin stop receiving chamber 82. Boss assembly region 78 is used to assemble articulating subcomponent 70 to boss 62. Because boss assembly region 78 is offset from channel 72, the possibility of accidental disassembly of articulating subcomponent 70 from base 60 is reduced. Accidental disassembly is further reduced as a result of the design of spin stop chamber loading region 80. Specifically, spin stop chamber loading region 80 is very narrow and tortuous. Thus, to become accidentally disassembled, articulating subcomponent 70 must translate and spin with respect to base 60 in a very specific pattern such that spin stop 64 translates within. The likelihood of such a pattern accidentally occurring is rather small.

Figure 17:
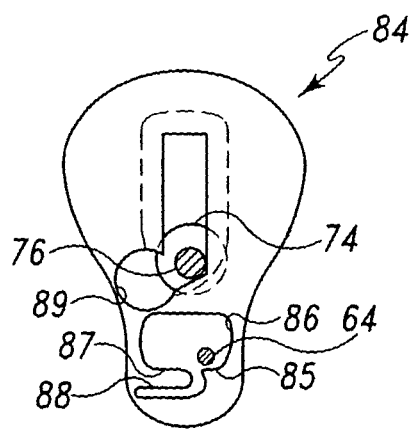
FIG. 17 is a bottom elevational view of an alternative embodiment of an articulating subcomponent of a patellar replacement component that incorporates features of the present invention that may be used with the base of FIG. 15.

Of course, it is possible to further reduce the likelihood of such accidental disassembly by further modification of the spin stop receiving chamber loading region. By way of example, FIG. 17 shows articulating subcomponent 84 with spin stop chamber 86 and spin stop chamber loading region 88. Spin stop chamber loading region 88 enters spin stop chamber 86 slightly to the right of center as viewed in FIG. 17. Moreover, spin stop chamber 86 is somewhat deeper at the lower right side than at the lower left side. Specifically, as shown in FIG. 17, wall 85 of spin stop chamber 86 is lower than wall 87. Consequently, accidental disassembly requires a very precise pattern of spin and translation such that spin stop 64 translates into spin stop chamber loading region 88, allowing boss 60 into boss assembly region 89.

Those of ordinary skill in the art will appreciate that the articulating subcomponents shown in FIGS. 16 and 17 may be easily modified to allow assembly onto bases of other shapes. By way of example, but not of limitation, by forming articulating subcomponents 70 or 84 with a flat bearing surface, they may be configured to be used with a base such as base 12 of FIG. 4.

Figure 18A:
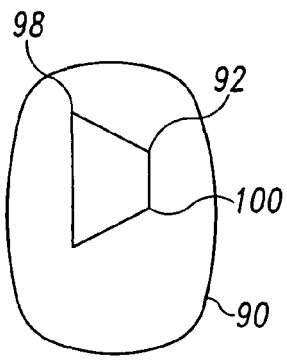
FIG. 18A is a top elevational view of an alternative embodiment of a base of a patellar replacement component that incorporates features of the present invention.
Figure 18B:
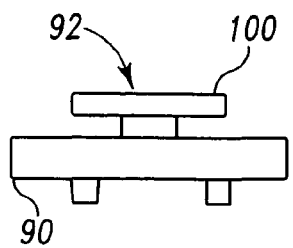
FIG. 18B is an end elevational view of the base of FIG. 18A.
Figure 19:
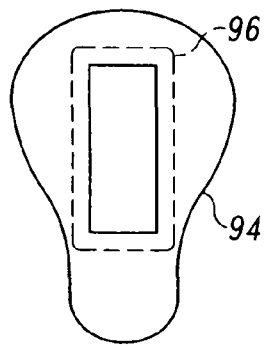
FIG. 19 is a bottom elevational view of an alternative embodiment of an articulating subcomponent of a patellar replacement component that incorporates features of the present invention that may be used with the base of FIG. 18A.

An alternative patellar replacement component is described with reference to FIGS. 18A, 18B and 19. Base 90 includes boss 92. The head of boss 92 is trapezoidal in shape. A trapezoidal head is very useful in providing a spin stop while reducing the number of parts in the component and simplifying production of the component. Specifically, as shown in FIG. 19, articulating subcomponent 94 includes channel 96 shown by dashed lines. The head of boss 92 is configured to fit within channel 96 and translation is allowed along the X-axis. Moreover, some rotation of articulating subcomponent 94 about boss 92 is possible since the width of the head of boss 92 is less than the width of channel 96.

Any such rotation or spin, however, is limited by the relative dimensions of the channel and the head of the boss. Specifically, relative motion is permitted until the boss contacts both sides of channel 96. In the embodiment of FIGS. 18A, 18B and 19, this occurs when, for example, corner 98 contacts one side of channel 96 and corner 100 contacts the opposing side of channel 96. This is because the length of the segment of the head of boss 92 between corner 98 and corner 100 is greater than the width of channel 96. Thus, the segment defined by corner 98 and corner 100 is a limiting segment since rotation is limited to one direction when corner 98 and corner 100 are athwart channel 96.

Those of ordinary skill in the relevant art will appreciate that a spin stop in accordance with the present invention may be realized in a number of different shapes. By way of example, but not of limitation, the spin stop may be in the shape of an ellipse, a rectangle, or a triangle. A single ellipse may be used to allow almost 180 degrees of spin by designing the ellipse with its major axis as the only limiting segment. A triangle may be designed to contact the sides of the channel with two combinations of corners. In other words, the head may be generally in the shape of a triangle having two sides longer than the third side, each of the longer sides being a limiting segment. A head may thus limit rotation from just less than 180 degrees to 5 degrees or less. Of course, providing other features on the boss that interact with channel features, such as areas of increased head height interacting with areas of increased channel depth, may also be used to provide a spin stop within the scope of the present invention.

Figure 20:
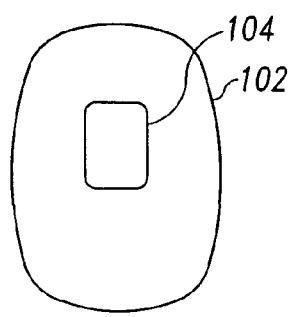
FIG. 20 is a top elevational view of an alternative embodiment of a base of a patellar replacement component that incorporates features of the present invention.
Figure 21:
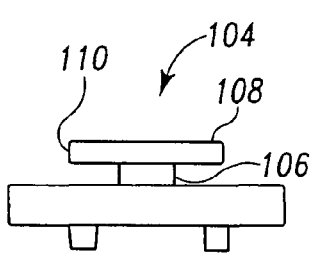
FIG. 21 is a side elevational view of the base of FIG. 20.
Figure 22:
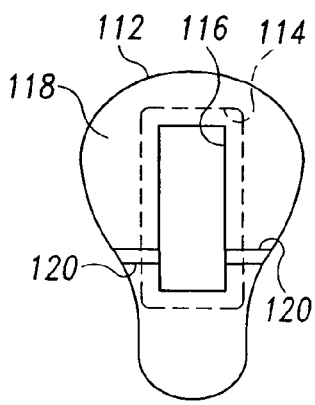
FIG. 22 is a bottom elevational view of an alternative embodiment of an articulating subcomponent of a patellar replacement component that incorporates features of the present invention that may be used with the base of FIG. 20.

Referring now to FIG. 20, an alternative boss is shown. Base 102 includes boss 104. As shown in FIG. 21, boss 104 includes stem 106 and head 108. Head 108 includes side 110. Referring now to FIG. 22, articulating subcomponent 112 includes channel 114 and lip 116. Lip 116 circumscribes the opening of channel 114 to bearing surface 118 and serves as a boss retaining member. Lip 116 includes boss assembly region 120. Boss assembly region 120 is an area of lip 116 that is made from a material that is more flexible than other portions of lip 116. By way of example, but not of limitation, lip 166 may be made of polyethylene of a certain density and boss assembly region 120 made from a less dense polyethylene. Thus, boss assembly region 120 is more easily deformed, allowing head 108 to be pushed into channel 114. Once head 108 is past boss assembly region 120, boss assembly region 120 flexes back to its original shape. Thus, head 108 is maintained in channel 114 by lip 116 and boss assembly region 120.

Figure 23:
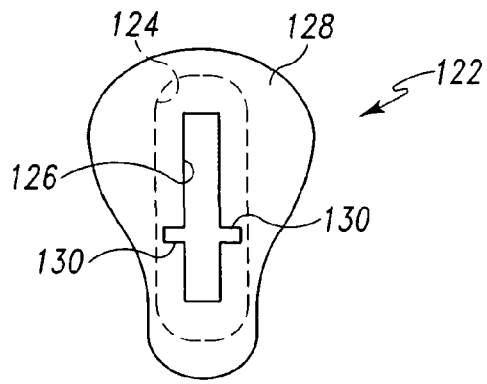
FIG. 23 is a bottom elevational view of an alternative embodiment of an articulating subcomponent of a patellar replacement component that incorporates features of the present invention that may be used with the base of FIG. 20.

An alternative boss assembly region that may be used with boss 104 is shown in FIG. 23. Articulating subcomponent 122 includes channel 124. Lip 126 substantially circumscribes the opening of channel 124 to bearing surface 128 of articulating subcomponent 122. Lip 126 in this embodiment is open at slot 130. Slot 130 is sized slightly shorter than the width of head 108 of boss 104. However, because lip 126 is made from a resilient material, such as polyethylene, head 108 may be forced through slot 130 and into channel 124. In the embodiment of FIG. 23, the width of slot 130 is selected to be approximately the same size as side 110 of boss 104 to provide additional ease in inserting head 108 into channel 124.

Figures 24, 25, 26A:
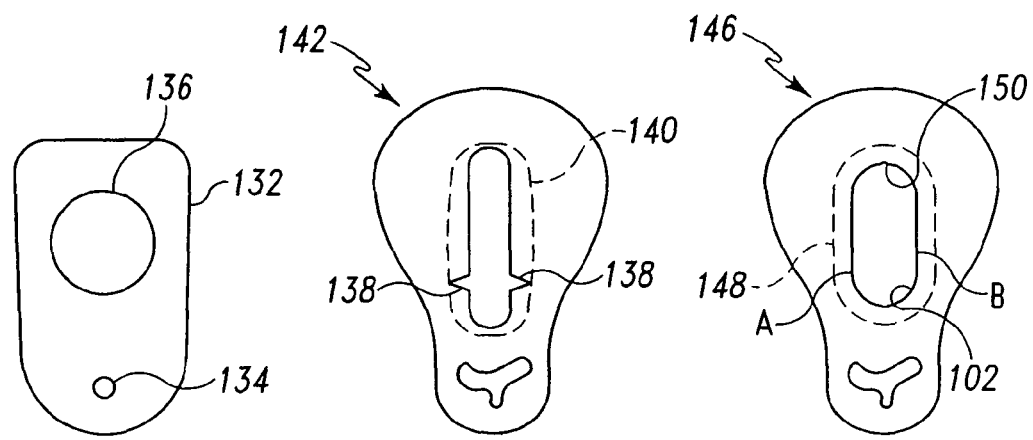
FIG. 24 is a top elevational view of an alternative embodiment of a base of a patellar replacement component that incorporates features of the present invention.
FIG. 25 is a bottom elevational view of an alternative embodiment of an articulating subcomponent of a patellar replacement component that incorporates features of the present invention that may be used with the base of FIG. 24.
FIG. 26A is a bottom elevational view of an alternative embodiment of an articulating subcomponent of a patellar replacement component that incorporates features of the present invention that may be used with the base of FIG. 24.

Referring now to FIG. 24, base 132 includes spin stop 134 and boss 136 which is dome shaped. Boss 136 thus has a cross section that is narrow at the edges and wider in the middle. Accordingly, slot 138 shown in FIG. 25 is triangularly shaped on each side of the opening of channel 140. Because slot 138 is narrow at its edges and wider toward the middle of slot 138, assembly of articulating subcomponent 142 onto boss 136 is accommodated. More specifically, because it is the cross section of the head of boss 136 that must pass through the boss assembly region, the shape of slot 138 is designed to substantially correspond with the cross section of the head of boss 136.

Figure 26B:
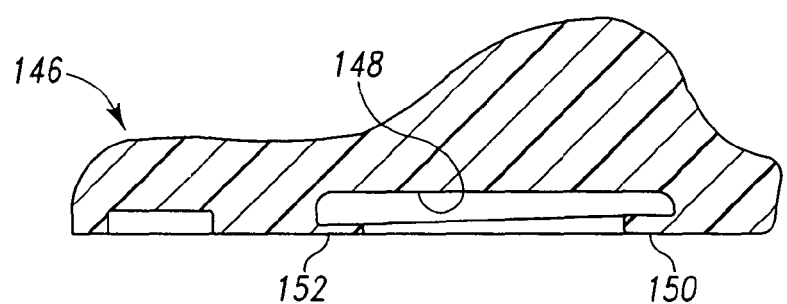
FIG. 26B is a cross sectional elevational view of the articulating subcomponent of FIG. 26A.

Yet another embodiment of a boss assembly region is shown in FIG. 26A. Articulating subcomponent 146 includes channel 148 substantially circumscribed by boss retaining region 150. In this embodiment, boss assembly region 152 which extends from point A to point B around the lower extremity of channel 148 is made of the same material as boss retaining region 150, which in this embodiment is polyethylene. However, as shown in FIG. 26B, boss assembly region 152 is substantially thinner than boss retaining region 150. Thus, boss assembly region 152 is more flexible than boss retaining region 150.

Figure 27A:
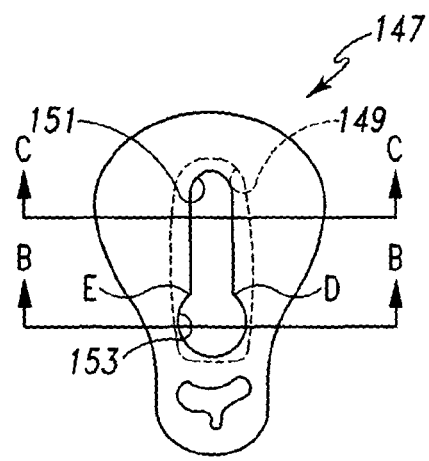
FIG. 27A is a bottom elevational view of an alternative embodiment of an articulating subcomponent of a patellar replacement component that incorporates features of the present invention that may be used with the base of FIG. 24.
Figure 27B:
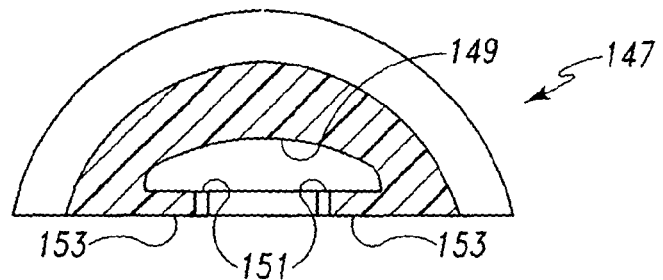
FIG. 27B is a cross sectional elevational view of the articulating subcomponent taken along line B-B of FIG. 27A.
Figure 27C:
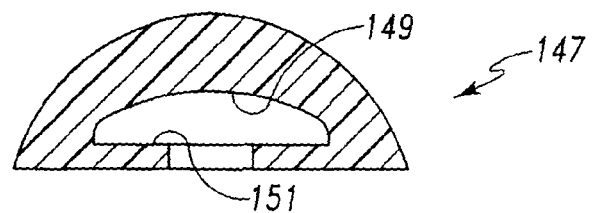
FIG. 27C is a cross sectional elevational view of the articulating subcomponent taken along line C-C of FIG. 27A.

FIG. 27A shows articulating subcomponent 147 which includes channel 149 substantially circumscribed by boss retaining region 151. In this embodiment, boss assembly region 153 which extends from point D to point E around the lower extremity of channel 149 is made of the same material as boss retaining region 151, which in this embodiment is polyethylene. However, boss assembly region 153 is configured with a lip that makes the opening to channel 149 from the bearing surface of articulating subcomponent 147 slightly smaller than the width of the head of the boss that is to be inserted into the channel. In contrast, boss retaining region 151 is configured with a lip that makes the opening to channel 149 from the bearing surface of articulating subcomponent 147 smaller than opening in boss assembly region 153. This is shown by comparison of FIG. 27B and FIG. 27C as boss assembly region 153 has a lip that extends over channel 149 less than the lip that extends over channel 149 in boss retaining region 151. Thus, boss assembly region 153 provides less resistance than boss retaining region 151 to movement of a head into or out of channel 149.

Figure 28A:
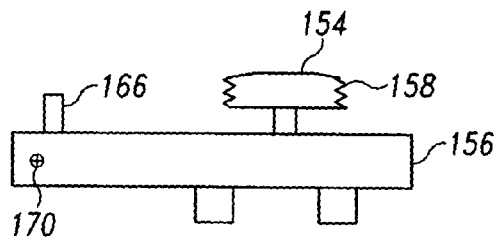
FIG. 28A is a side elevational view of an alternative embodiment of a base of a patellar replacement component that incorporates features of the present invention.
Figure 29:
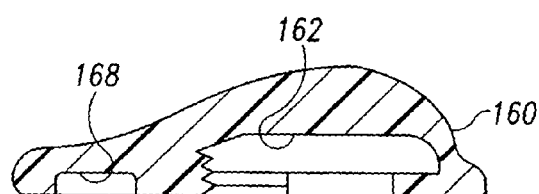
FIG. 29 is a cross sectional elevational view of an alternative embodiment of an articulating subcomponent of a patellar replacement component that incorporates features of the present invention that may be used with the base of FIG. 28A.
Figure 30:
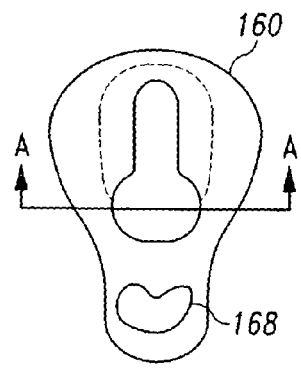
FIG. 30 is a bottom elevational view of the articulating subcomponent of FIG. 29.
Figure 31:
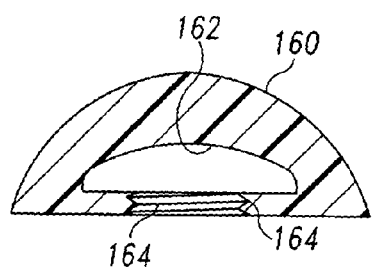
FIG. 31 is a cross sectional elevational view taken along line A-A of FIG. 30.

According to another embodiment of the invention, the boss is keyed to fit within the channel in a specific manner. Referring to FIG. 28A, boss 154 of base 156 includes head 158. Head 158 is threaded. Articulating subcomponent 160 includes channel 162 and boss assembly region 164 as shown in FIG. 29. Boss assembly region 164 is threaded so as to engage threaded head 158. This is also shown in FIG. 31 which a cross sectional view of articulating subcomponent 160 taken along line A-A of FIG. 30.

Figure 28B:
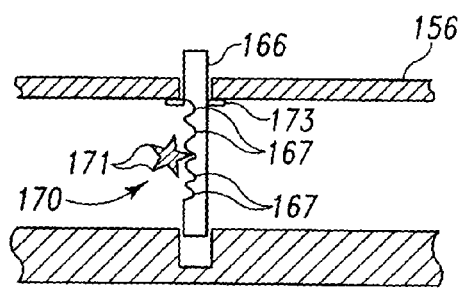
FIG. 28B is a partial side cross sectional view of the retractable spin stop and retracting screw of FIG. 28A.

Base 156 of FIG. 28A further includes spin stop 166 which is received within spin stop receiving chamber 168. Spin stop 166 in this embodiment is movable into base 156. As shown in FIG. 28B, spin stop 166 includes a plurality of notches 167. Retracting screw 170 includes a plurality of fins 171 configured to engage notches 167 of spin stop 166. Thus, rotation of retracting screw 170 in a clockwise direction retracts spin stop 166 into base 156. Specifically, fins 171 engage notches 167 forcing spin stop to move in a downward direction. Once spin stop 166 is moved into base 156, articulating subcomponent 160 may be freely rotated with respect to boss 154.

Rotation of retracting screw 170 in a counterclockwise direction causes fins 171 to engage notches 167, forcing spin stop 166 to move out of base 156. Upward movement of spin stop 166 is constrained by restraining flange 173 contacting the underside of the upper surface of base 156.

Thus, assembly of articulating subcomponent 160 to base 156 begins by retracting spin stop 166 into base 156. Articulating subcomponent 160 is then located above boss 154 such that boss 154 is adjacent to boss assembly region 164. Articulating subcomponent 160 is then rotated such that the threads of boss assembly region 164 engage the threads of head 158. Rotation is continued until head 154 is within channel 162 and the threads on head 158 are no longer engaged with the threads of boss assembly region 164. Spin stop receiving chamber 166 is then moved to a position above retracted spin stop 166, and spin stop 166 is advanced into spin stop receiving chamber 166 by turning retracting screw 170 as discussed above.

Use of a spin stop that is retractable into the base of a patellar replacement component thus provides assured assembly following a simple method, virtually eliminating accidental disassembly. Moreover, while the threading of head 158 and boss assembly region 164 requires more than one complete revolution to insert head 158 past boss assembly region 164, such an amount of rotation is not required to realize assured assembly.

Figure 32A:
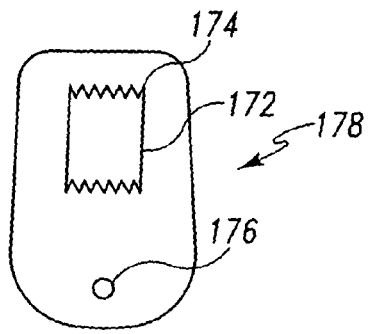
FIG. 32A is a top elevational view of a base of a patellar replacement component that incorporates features of the present invention with a keyed head.
Figure 32B:
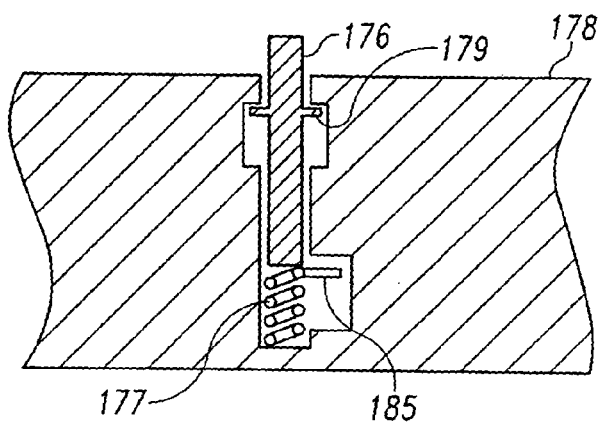
FIG. 32B is a cross sectional elevational view of the spring loaded spin stop of FIG. 32A.
Figure 33:
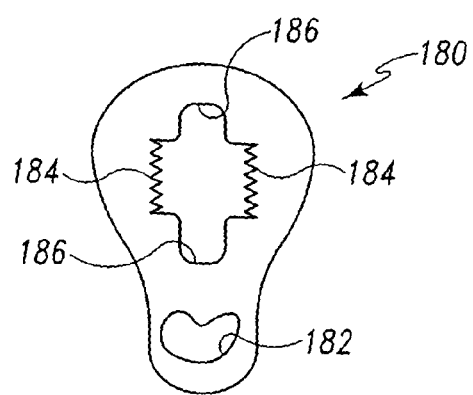
FIG. 33 is a bottom elevational view of an articulating subcomponent of a patellar replacement component that incorporates features of the present invention with a keyed boss loading region that may be used with the base of FIG. 32A.

By way of example, boss 172 shown in FIG. 32A includes keyed head 174 and movable spin stop 176. As shown in FIG. 32B, spin stop 176 is located above spring 177. Spring 177 is a biasing member configured to bias spin stop 176 in a direction out of boss 172. Thus, by pressing on spin stop 176, it may be forced against spring 177, compressing spring 177 as it moves into plate 178. When released, spring 177 forces spin stop 176 out of plate 178 until upward movement of spin stop 176 is constrained by flange 179. Articulating subcomponent 180 shown in FIG. 33 includes spin stop receiving chamber 182 and boss assembly region 184 surrounded by boss retaining region 186.

Assembly of articulating subcomponent 180 onto base 178 is provided for as boss assembly region 184 and head 174 are complimentarily keyed such that when articulating subcomponent 180 is rotated 90 degrees to the right and inverted, head 174 will pass through boss assembly region 184. By moving spin stop 176 into base 178, articulating subcomponent 180 may then be rotated into an assembled position above base 178. Release of spin stop 176 allows spin stop 176 to move out of base 178 and into spin stop receiving chamber 182. Because 90 degrees of rotation is not allowed when spin stop 176 is within spin stop receiving chamber 182, the assembled patellar replacement component will not become accidentally disassembled.

Figure 32C:
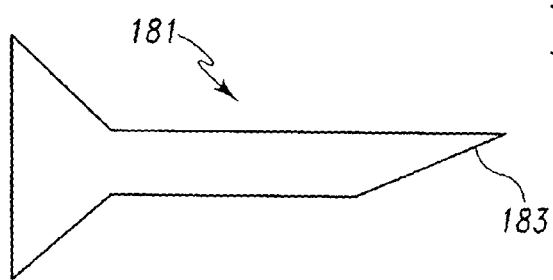
FIG. 32C is a side elevational view of a key used to retract the spin stop of FIG. 32A into the base of FIG. 32A.

Removal of articulating subcomponent 180 during replacement is very simple. A surgeon merely inserts key 181, shown in FIG. 32C, into a slot (not shown) in the side of base 178. As key 181 is inserted, ramp 183 engages compressing bar 185, forcing compressing bar 185 downward. Thus, spring 177 is compressed and spin stop 176 is moved into base 178. Articulating subcomponent 180 is then rotated 90 degrees such that the keyed head 174 mates with the keyed boss assembly region 184, and the articulating subcomponent 180 is removed from base 178. Thus, spin stop is made retractable by provision of key 181 and compressing bar 185.

Figure 34:
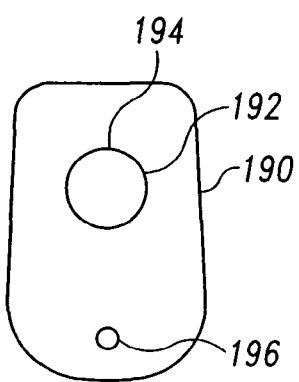
FIG. 34 is a top elevational view of a base of a patellar replacement component that incorporates features of the present invention with a movable spin stop.
Figure 35:
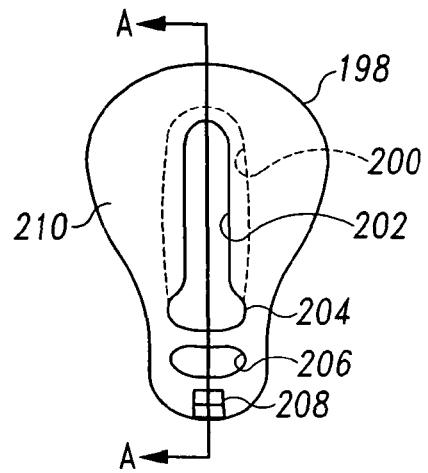
FIG. 35 is a bottom elevational view of an articulating subcomponent of a patellar replacement component that incorporates features of the present invention that may be used with the base of FIG. 34.
Figure 36A:
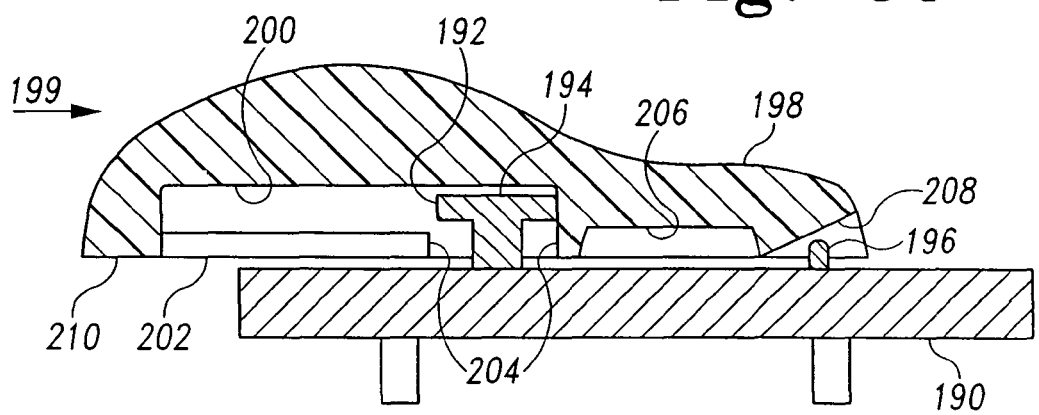
FIGS. 36A and 36B are cross sectional elevational views of the articulating subcomponent of FIG. 35 being assembled onto the base of FIG. 34.

Assembly of a patellar replacement component in accordance with the present invention may be even further simplified. With reference to FIGS. 34-35, base 190 includes boss 192 having head 194 and movable spin stop 196 which may be, by way of example, spring loaded as shown in FIG. 32B or retractable as shown in FIG. 28B. Articulating subcomponent 198 includes channel 200 substantially surrounded by boss retaining lip 202 and boss assembly region 204. Spin stop receiving chamber 206 is located adjacent boss assembly region 204. Articulating subcomponent 198 also includes ramp area 208. As shown in FIG. 36A, ramp area 208 is nearly co-planar with bearing surface 210 near spin stop receiving chamber 206, and at the opposite end has a depth approximately equal to the height of spin stop 196 when spin stop 196 is not moved into base 190.

Figure 36B:
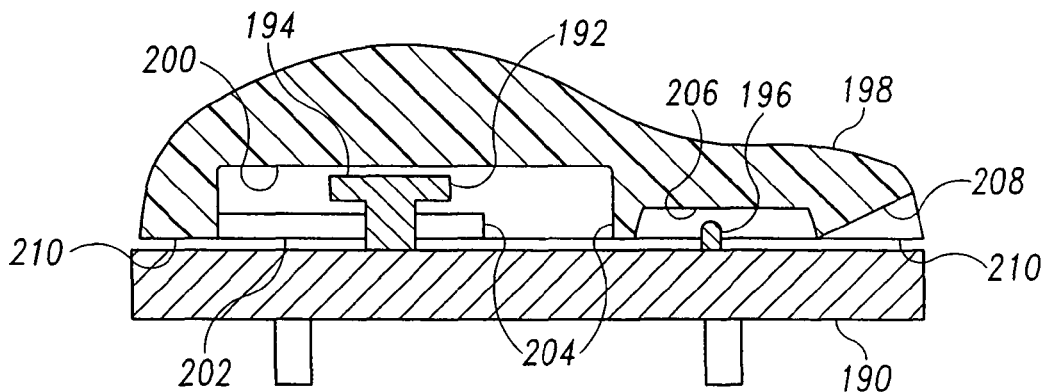

Assembly of articulating subcomponent 198 onto base 190 is described with reference to FIGS. 36A and 36B. Articulating subcomponent 198 is initially placed on base 190 as shown in FIG. 36A. Head 194 is thus inserted into boss assembly region 204 which is about the same width as head 194. At this point, spin stop receiving chamber 206 is located above the surface of base 190 and between boss 192 and spin stop 196. Spin stop 196 is located beneath ramp area 208.

Articulating subcomponent 198 is then moved in the direction of arrow 199. Consequently, head 194 of boss 192 moves within channel 200 and above retaining lip 202. As ramp area 208 contacts spin stop 196, spin stop 196 is pressed into base 190. Movement in the direction of arrow 199 continues until spin stop receiving chamber 206 is located above spin stop 196 at which time spin stop 196 moves out of base 190 and into spin stop receiving chamber 206 as shown in FIG. 36B. At this time, head 194 is maintained within channel 200 by retaining lip 202. Moreover, head 194 cannot move back into boss assembly area 204 when spin stop 196 is within spin stop receiving chamber 206. Specifically, spin stop 196 contacts the rear wall of spin stop receiving chamber 206 while head 194 is still above retaining lip 202. Thus, the potential for accidental disassembly is minimized.

Figure 37:
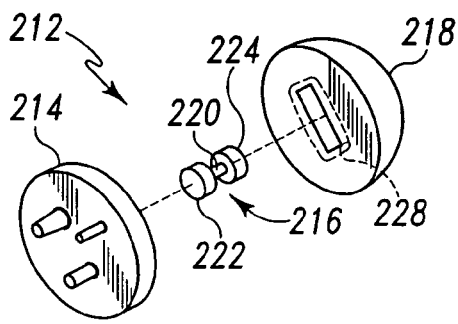
FIG. 37 is an exploded perspective view of an alternative patellar replacement component that incorporates features of the present invention.

While the foregoing examples have shown bosses that are rigidly attached to the base, the present invention is not so limited. The boss may, if desired, be movably attached to the base with the boss either fixedly or movably attached to the articulating subcomponent. By way of example, FIG. 37 is an exploded view of an alternative embodiment of a patellar replacement component. Patellar component 212 includes base 214, boss 216 and articulating subcomponent 218. Boss 216 is generally in the shape of a barbell, having a narrow stem 220 and two enlarged heads 222 and 224. Heads 222 and 224 are configured to fit within channels 226 of base 214 and 228 of articulating subcomponent 218 respectively, see FIG. 38. Heads 222 and 224 may be inserted and retained within channels 226 and 228 in accordance with methods discussed above with respect to other embodiments. Additionally, heads 222 and 224 may be configured along with channels 226 and 228 to allow for limited rotation in accordance with the bosses and channels described above. Thus, patella replacement component 212 includes the ability to translate along the X and the Y-axis as well as the freedom to spin about the Z-axis.

Figure 38:
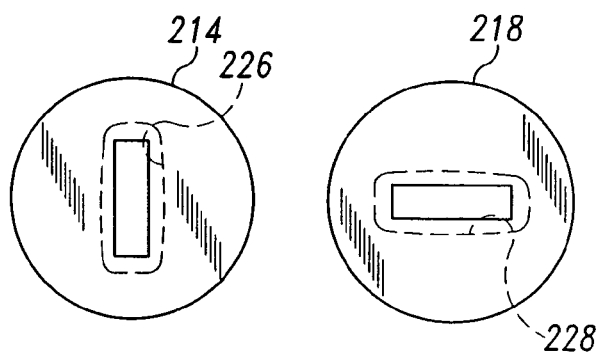
FIG. 38 is an elevational laid open view of the top of the base and the bottom of the articulating subcomponent of FIG. 37.

If it is desired to have three degrees of rotation, the embodiment of FIGS. 37 and 38 may be modified so as to have a curved interface such as that described above with reference to FIGS. 15 and 16. Thus, if base 214 is dome shaped, then channel 226 allows for rotation about the X-axis and channel 228 allows for rotation about the Y-axis. Z-axis spin may be provided for as discussed above with reference to FIG. 37.

Figure 39:
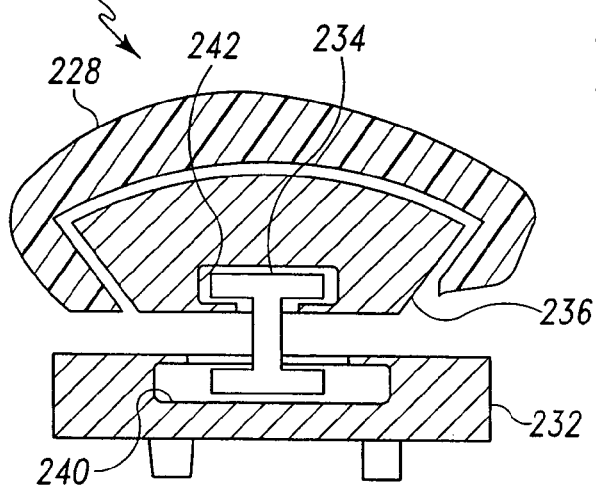
FIG. 39 is a cross sectional view of an alternative patellar replacement component that incorporates features of the present invention.
Figure 40:
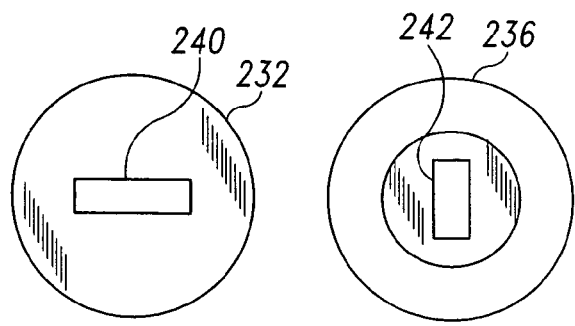
FIG. 40 is an elevational laid open view of the top of the base and the bottom of the articulating base of FIG. 39.

The embodiment shown in FIGS. 39-40 allows for unconstrained spin about the Z-axis. Patellar replacement component 230 includes base 232, boss 234, articulating base 236 and bone contacting component 238. Base 232 and articulating base 236 include channels 240 and 242 respectively as shown in FIG. 40. Accordingly, X and Y-axis translation is provided for as in the embodiment of FIGS. 37-38. However, bone contacting component 238 is free to spin completely around articulating base 236. Of course, three degrees of rotation may be provided by configuring base 232 and the lower part of articulating base 234 in a dome shape.

Figure 41:
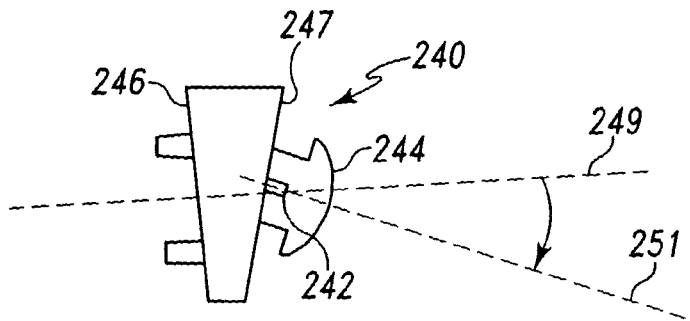
FIG. 41 is a side elevational view of an alternative patellar replacement component base that incorporates features of the present invention.

Improved tracking of a patellar replacement component may be further realized by modifying the angle of the bone contacting surface of the articulating component with respect to the angle defined by the quadriceps tendon and the patellar tendon of the resected patella. With reference to FIG. 41, base 240 includes spin stop 242, boss 244, bone contacting surface 246 and articulating component contact surface 247. Bone contacting surface 246 of base 240 has a width that decreases from top to bottom as viewed in FIG. 41. Thus, bone contacting surface 246 lies generally in a plane that generally conforms to the plane of the patellar resection. Accordingly, an axis that is orthogonal to the plane of bone contacting surface may be referred to as an axis of resection. This is shown in FIG. 41 by resection axis 249.

Figure 42:
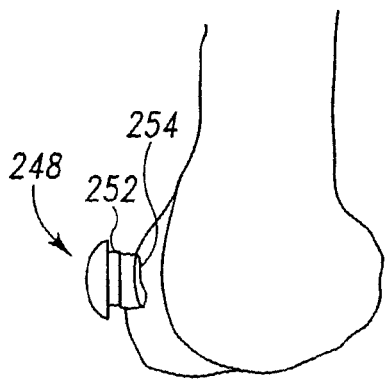
FIG. 42 is a perspective view showing the orientation of a bone articulating surface of a patellar replacement component with respect to a femur.
Figure 43:
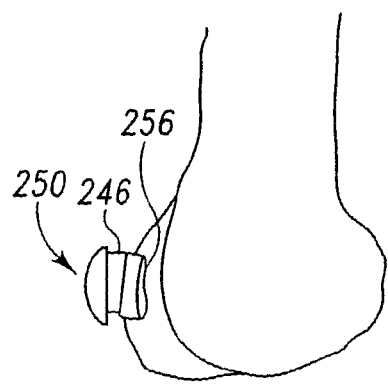
FIG. 43 is a side perspective view showing the orientation of a bone articulating surface of a patellar replacement component using the base of FIG. 41 with respect to a femur.
Figure 44:
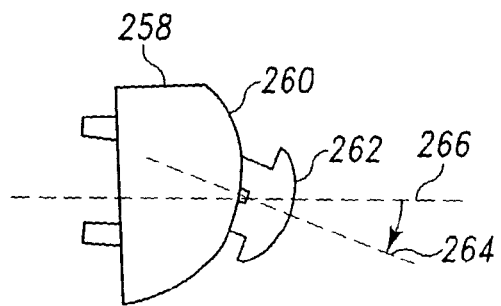
FIG. 44 is a side elevational view of an alternative patellar replacement component base that incorporates features of the present invention.

Articulating component contact surface 247 in this embodiment also defines a plane. An axis orthogonal to the articulating component contact surface 247 is shown by axis 251. Axis 251 is rotated with respect to resection axis 249. The angle is selected so as to such that the bone contacting surface of an articulating component assembled onto base 246 will contact a femur at an angle that more closely resembles a natural patella. This is shown by comparing patellar replacement component 248 in FIG. 42 with patellar replacement component 250 shown in FIG. 43. Patellar replacement component 248 includes base 252 that is of a uniform depth. In contrast, base articulating component 250 includes base 246 which has a depth that decreases from top to bottom as viewed in FIG. 41. Thus, as compared with bone contacting surface 254 of patellar replacement component 248, bone contacting surface 256 of patellar replacement component 250 is rotated in a clockwise direction.

Figure 45:
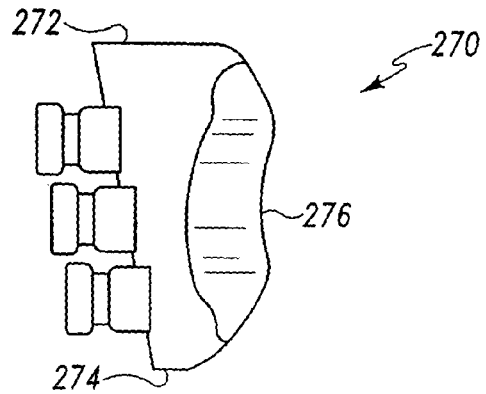
FIG. 45 is a side elevational view of an alternative embodiment of an articulating subcomponent of a patellar replacement component that incorporates features of the present invention.

An alternative embodiment of a patellar replacement component is shown in FIG. 45. Patellar replacement component 270 is a single piece component constructed entirely of polyethylene. Patellar replacement component 270 is thicker at superior portion 272 than at inferior portion 274. Thus, articulating surface 276 will contact a femur at an angle that more closely resembles a natural patella.

Base 240 or patellar replacement component 270 may be used when resection of a patella is performed in accordance with known methods using, for example, patellar replacement component provided as a kit including left patellar replacement components and right patellar replacement components. Separately designed left and right patellar replacement component are needed because the replacement components in these embodiments are not symmetrical. Therefore, proper orientation of the articulating surface requires unique components for the right and left knee.

Alternatively, a new method of resection may be followed which allows the use of patellar replacement component having a base of a uniform depth. In accordance with this new method, an image is taken of the patella to be replaced. Based upon this imagery, an optimal resection angle is generated. A surgeon may then use a traditional cutting guide attached to the quadriceps tendon and the patellar tendon, and angle the patellar resection off of the cutting guide in accordance with the generated angle. To improve the accuracy of the resection, the resection may be performed as image guided surgery, allowing the surgeon to make corrections to the resection as needed.

Alternatively, a traditional cutting guide may be modified to allow the guide surface to be angled with respect to the angle defined by the quadriceps tendon and the patellar tendon. Accordingly, after an image is taken and a modified angle is determined, the guide surface is adjusted from the angle defined by the quadriceps tendon and the patellar tendon to the optimized angle.

Those of ordinary skill in the art will appreciate that the above new methods and/or the use of a patellar replacement component having a base of varying depth may be combined with the other features of the present invention discussed above. By way of example, but not of limitation, base 258 includes domed articulating surface 260 which is generally opposite bone contacting surface 262. In this embodiment, the orientation of bone contacting surface of the articulating component is a function of the orientation of the stem of boss 262. Thus, an axis is defined by a line drawn axially through the center of the stem of boss 262 shown as axis 264. Axis 264 is rotated with respect to resection axis 266.

Figure 46A:
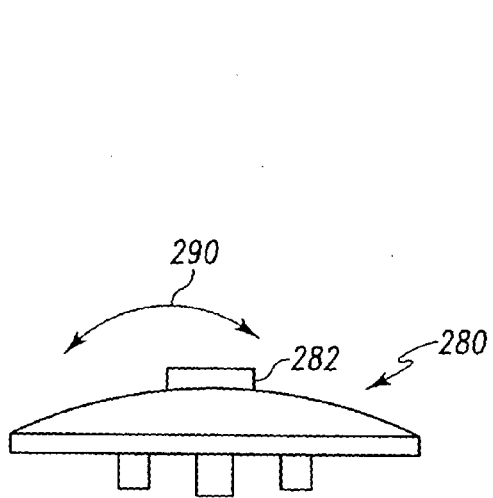
FIG. 46A is a top elevational of an alternative embodiment of a base of a patellar replacement component that incorporates features of the present invention.
Figure 46B:
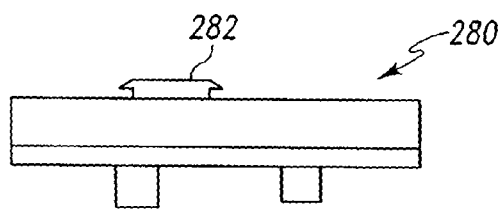
FIG. 46B is a side elevational view of the base of FIG. 46A.
Figure 46C:
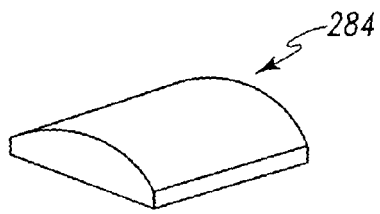
FIG. 46C is a perspective elevational view of a base having a shape similar to the shape of the base of FIG. 46A.

Another patellar replacement component incorporating features of the present invention is shown in FIGS. 46A-47B. FIG. 46A shows base subcomponent 280 and boss 282 from a top elevational view. Base subcomponent 280 is curved along the X-axis. As shown in FIG. 46B, which is a side elevational view, base subcomponent 280 is not curved along the Y-axis. Thus, base subcomponent 280 is generally in the shape of a portion of a side of a tube or barrel. This shape is shown more clearly in the perspective view of base subcomponent 284 shown in FIG. 46C.

Figure 47A:
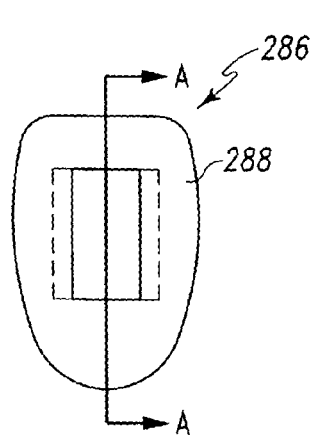
FIG. 47A is a bottom elevational view of an articulating subcomponent of a patellar replacement component that incorporates features of the present invention that may be used with the base of FIG. 46A.
Figure 47B:
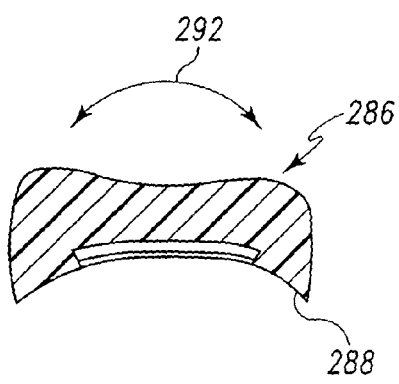
FIG. 47B is a cross sectional view taken along line A-A of FIG. 47A.

Articulating subcomponent 286 shown in FIG. 47A may be used with base subcomponent 280. As shown in FIG. 47B, articulating subcomponent 286 is curved along bearing surface 288 in a complimentary fashion to the curve of base subcomponent 280. Accordingly, articulating component 286 is allowed to move along base subcomponent 280 in the manner indicated by arrows 290 and 292 of FIGS. 46A and 47B, respectively. This movement results in rotation about the Y-axis.

Figure 48A:
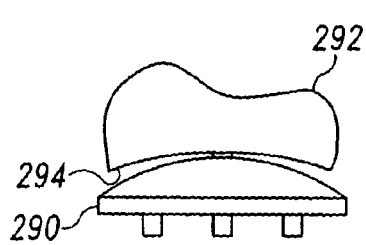
FIG. 48A is a side elevational view of an alternative embodiment of a patellar replacement component incorporating features of the present invention.
Figure 48B:
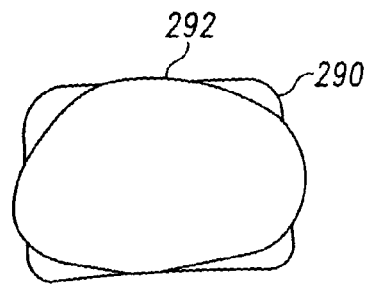
FIG. 48B is a front elevational view of the patellar replacement component of FIG. 48A.
Figure 48C:
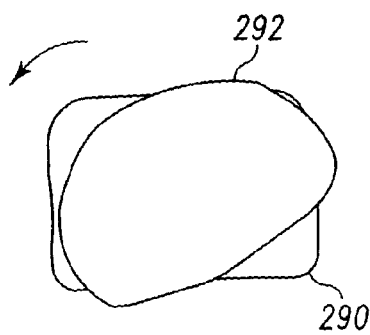
FIG. 48C is a view similar to FIG. 48B, but shows the articulating subcomponent of the patellar replacement component after spinning.

If desired, base subcomponent 280 and/or articulating subcomponent 286 may be modified to further allow rotation about the Z-axis. Such a configuration is shown in FIGS. 48A-D. As shown in FIG. 48A, base subcomponent 290 is similar to base 280 of FIG. 46A. However, articulating subcomponent 292 includes bearing surface 294 which is less curved than the top of base subcomponent 290. FIG. 48B is a front elevational view of articulating subcomponent 292 and base subcomponent 290 with the same orientation as shown in FIG. 48A. Because bearing surface 294 is only in contact with base subcomponent 290 at one point as shown in FIG. 48A, spin about the Z-axis is allowed.

Figure 48D:
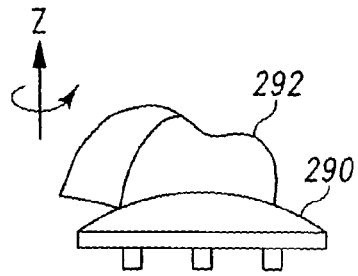
FIG. 48D is a view similar to FIG. 48A, but shows the articulating subcomponent of the patellar replacement component after spinning.

Base subcomponent 290 in this embodiment acts as a spin stop. When articulating subcomponent 292 spins to the position shown in FIG. 48C, bearing surface 294 contacts base subcomponent at a second point as shown in FIG. 48D. Accordingly, articulating subcomponent 292 is not allowed to continue to spin in the same direction.

Figure 49A:
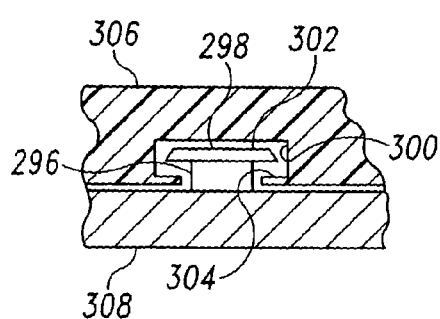
FIG. 49A is a partial cross-sectional view of an alternative embodiment of a patellar replacement component incorporating features of the present invention.
Figure 49B:
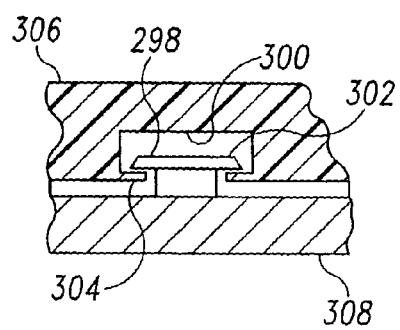
FIG. 49B is similar to FIG. 49A but shows the articulating component and base subcomponent after spinning.

Additionally and/or alternatively, the stem of the boss and the channel of the articulating subcomponent may be modified to allow spin. As shown in FIG. 49A, stem 296 of boss 298 is elongated. The depth of channel 300 is complimentarily increased to allow head 302 to be located well above boss retaining lips 304. Accordingly, as articulating subcomponent 306 spins and contacts base subcomponent 308, in a manner similar to articulating subcomponent 292 and base subcomponent 290 shown in FIG. 48D, the contact generates a force that attempts to push base subcomponent 308 away from articulating subcomponent 306 and allow additional spin. Because there is space between boss retaining lips 302 and head 300, articulating subcomponent 306 is allowed to spatially separate from base subcomponent 308 and additional spin is allowed. This continues until boss retaining lips 302 contact head 302 as shown in FIG. 49B. At this point, additional spin is not allowed. Thus, boss 298 functions as a spin stop and channel 300 functions as a spin stop receiving chamber.

Those of ordinary skill in the relevant art will appreciate that the invention described above provides for a patellar replacement component that presents fewer patella femoral complications following a total knee replacement or a partial knee replacement. In accordance with the present invention, the patellar kinematics of the replacement components more closely resemble the kinematics with natural bones, allowing increase flexion while reducing patellar clunk syndrome. Moreover replacement components in accordance with the present invention present lower contact stresses, resulting in extended replacement component life.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:
1. A patellar prosthesis comprising:
a first subcomponent;
a boss operably connected to the first subcomponent; and
a second subcomponent movably connected to the first subcomponent with the boss, the second subcomponent comprising,
a first side in opposition to the first subcomponent, the first side having (i) a channel opening to and encompassed by the first side, (ii) a boss retaining region operable to retain the boss within the channel when the boss is inserted into the channel by contacting the boss, and (iii) a boss assembly region operable to facilitate the insertion of the boss into the channel, by allowing the boss to pass through the boss assembly region for insertion of the boss into the channel,
wherein:
the boss comprises a stem and a head having a width;
the channel has a first side and a second side, the second side spaced apart from the first side by a first distance; and
the boss retaining region comprises a lip, a first section having a width and a second section having a width, the first section of the lip located on the first side of the channel and the second section of the lip located on the second side of the channel, the width of the head being greater than the first distance of the channel minus the width of the first section of the lip and minus the width of the second section of the lip.
2. The patellar prosthesis of claim 1, wherein the first subcomponent comprises a base and wherein the second subcomponent comprises an articulating subcomponent.

3. The patellar prosthesis of claim 1, further comprising:
a spin stop operably connected to the first subcomponent, and wherein the second subcomponent further comprises:
a spin stop receiving chamber, the spin stop receiving chamber configured to receive the spin stop when the second subcomponent, boss and first subcomponent are assembled, such that the spin stop is movable solely within the spin stop receiving chamber and the boss cannot move within the spin stop receiving chamber.

4. The patellar prosthesis of claim 1, wherein the boss assembly region opens to the first side and is offset from the channel along the first side.

5. The patellar prosthesis of claim 4, further comprising:
a spin stop operably connected to the first subcomponent, and wherein the second subcomponent further comprises:
a spin stop receiving chamber with a loading region, the loading region of the spin stop chamber configured such that when the boss is being inserted into the channel through the boss assembly region, the spin stop is inserted into the spin stop chamber loading region.

6. A patellar replacement component base comprising:
a generally planar bone contacting surface defining a first plane;
a dome shaped contact surface for contacting a patellar articulating component and located generally opposite the bone contacting surface; and
a boss having a stem extending from the dome shaped articulating component contact surface along an axis, the axis of the stem intersecting the first plane at an angle of other than 90 degrees.

7. The patellar replacement component base of claim 6, further comprising:
a spin stop extending from the dome shaped contact surface along a spin stop axis, the spin stop axis intersecting the bone contacting surface plane at an angle of other than 90 degrees.

8. The patellar replacement component base of claim 7, wherein:
the dome shaped contact surface forms an apex; and
the spin stop and the boss are on opposite sides of the apex when viewed from a side elevational view.

9. The patellar replacement component base of claim 7, wherein:
the boss includes a head portion extending outwardly from the stem portion, the head portion extending over a portion of the contact surface; and
the spin stop is cylindrically shaped.

10. The patellar replacement component base of claim 6, wherein the dome shaped contact surface is spherical.

11. A patellar prosthesis comprising:
a first subcomponent;
a boss operably connected to the first subcomponent; and
a second subcomponent movably connected to the first subcomponent with the boss, the second subcomponent comprising,
a first side, the first side in opposition to the first subcomponent and having (i) a channel extending inwardly therefrom, (ii) a boss retaining region having a first configuration operable to retain the boss within the channel when the boss is inserted into the channel by contacting the boss, and (iii) a boss assembly region encompassed by the first side and having a second configuration operable to facilitate the insertion of the boss into the channel, the first configuration and the second configuration being different, wherein:
the boss comprises a stem and a head having a width;
the channel has a first side and a second side, the second side spaced apart from the first side by a first distance; and
the boss retaining region comprises a lip, a first section having a width and a second section having a width, the first section of the lip located on the first side of the channel and the second section of the lip located on the second side of the channel, the width of the head being greater than the first distance of the channel minus the width of the first section of the lip and minus the width of the second section of the lip.

12. The patellar prosthesis of claim 11, wherein the first subcomponent comprises a base and wherein the second subcomponent comprises an articulating subcomponent.

13. The patellar prosthesis of claim 11, further comprising:
a spin stop operably connected to the first subcomponent, and wherein the second subcomponent further comprises:
a spin stop receiving chamber, the spin stop receiving chamber configured to receive the spin stop when the second subcomponent, boss and first subcomponent are assembled, such that the spin stop is movable solely within the spin stop receiving chamber and the boss cannot move within the spin stop receiving chamber.

14. The patellar prosthesis of claim 11, wherein the boss assembly region is connected to but offset from the channel.

15. The patellar prosthesis of claim 14, further comprising:
a spin stop operably connected to the first subcomponent, and wherein the second subcomponent further comprises:
a spin stop receiving chamber with a loading region, the loading region of the spin stop chamber configured such that when the boss is being inserted into the channel through the boss assembly region, the spin stop is inserted into the spin stop chamber loading region.

16. A patellar replacement component base comprising:
a body defining (i) a generally planar bone contacting surface defining a first plane, and (ii) a dome shaped articulating component contact surface generally opposite the bone contacting surface;
a stem extending outwardly from the dome shaped articulating component contact surface of said body along a line, the line of the stem intersecting the first plane at an angle of other than 90 degrees; and
a head extending from said stem.

17. The patellar replacement component base of claim 16, wherein said body, said stem, and said head are integral with each other.

18. The patellar replacement component base of claim 16, wherein said body, said stem, and said head are made of a polymer.

19. A patellar replacement component base comprising:
an integral body defining generally planar bone contacting surface defining a first plane, the integral body including a dome shaped contact surface generally opposite the bone contacting surface; and
a stem extending outwardly from the dome shaped contact surface of said body in a direction away from the generally planar bone contacting surface along an axis, the axis of the stem intersecting the first plane at an angle of other than 90 degrees, the stem being integral with said body.

20. The patellar replacement component base of claim 19, further comprising a head extending from said stem.

21. The patellar replacement component base of claim 19, wherein said body and said stem are made of a polymer.

* * * * *